United States Patent [19]

Braden et al.

[11] 4,002,673
[45] Jan. 11, 1977

[54] PROCESS FOR THE PREPARATION OF UNSATURATED AMINO COMPOUNDS

[75] Inventors: Rudolf Braden, Odenthal-Scheuren; Hans Knupfer, Schlidgen; Sigurd Hartung, Cologne, all of Germany

[73] Assignee: Bayer Aktiengesellschaft, Leverkusen, Germany

[22] Filed: Dec. 12, 1974

[21] Appl. No.: 532,184

[30] Foreign Application Priority Data

May 28, 1974 Germany .......................... 2425811

[52] U.S. Cl. .......................... 260/510; 260/326 N; 260/326.12 R; 260/315; 260/465 E; 260/471 R; 260/508; 260/518 R; 260/558 A; 260/561 N; 260/576; 260/580; 260/586 R

[51] Int. Cl.² ................. C07C 143/56; C07C 85/11

[58] Field of Search ....... 260/510, 508, 580, 471 R

[56] References Cited

UNITED STATES PATENTS

| | | | |
|---|---|---|---|
| 2,402,439 | 6/1946 | Owen | 260/580 |
| 2,547,910 | 4/1951 | Hausermann et al. | 260/510 |
| 3,350,450 | 10/1967 | Dovell et al. | 260/580 |
| 3,506,657 | 4/1970 | Hausermann | 260/510 |
| 3,761,425 | 9/1973 | Baessler et al. | 260/580 |

OTHER PUBLICATIONS

Broadbent, et al., J. Am. Chem. Soc., 76, 1519 (1954).
Rose, et al., The Condensed Chemical Dictionary, 5th Edition, pp. 233–244 (1956).

*Primary Examiner*—James O. Thomas, Jr.
*Assistant Examiner*—Nicky Chan.
*Attorney, Agent, or Firm*—Plumley and Tyner

[57] ABSTRACT

Process for the preparation of aromatic amines which additionally still contain C-C multiple bonds, characterized in that aromatic nitro compounds which still contain C-C multiple bonds are hydrogenated in the presence of metal sulphides of the formula $MeS_x$ in which $x$ is a number from 1 to 4 and Me represents a metal atom of the group consisting of iron, nickel, ruthenium, rhodium, palladium, rhenium, osmium, iridium and platinum as catalysts, at 20° to 140° C and at 5 to 150 bars hydrogen pressure.

7 Claims, No Drawings

PROCESS FOR THE PREPARATION OF UNSATURATED AMINO COMPOUNDS

The subject of the invention is a process for the preparation of aromatic amino compounds which still contain C-C multiple bonds, by selective catalytic reduction of aromatic nitro compounds which still contain C-C multiple bonds.

There has hitherto not been a generally industrially applicable process for the selective catalytic reduction of nitro groups present alongside olefine bonds. In particular, the selective catalytic reduction of nitro groups alongside monosubstituted or disubstituted or activated olefine bonds has hitherto not been solved industrially.

Nitro compounds prepared industrially frequently contain impurities, originating from the process of preparation, which only permit catalytic hydrogenation, on noble metal catalysts or Raney catalysts, at elevated temperature and using a large amount of catalyst. Since the selectivity of a catalyst decreases greatly with increasing temperature, even slightly contaminated industrial nitro compounds containing olefine groups are no longer selectively reduced on nickel catalysts or noble metal catalysts. Even small amounts of Na cyanide, Na sulphide, Na bisulphite or Na sulphite completely inhibit the hydrogenation of a nitro group on Pd contact catalysts (H. Greenfield, J. org. Chem. 28, 2434 (1963)).

Hitherto, only few examples of an aromatic nitro group being reduced selectively alongside a monosubstituted double bond have become known. 3-Nitrostyrene has been reduced to 3-aminostyrene, with 17% yield, by means of a rhenium catalyst at 200 bars of $H_2$ and 135° C (M. Freifelder: Practical Catalytic Hydrogenation, New York 1971, page 193). Broadbent and Seegmüller report on the reduction of nitrostyrene to m-aminostyrene on $ReO.2H_2O$ as the catalyst. This catalyst can only be prepared by expensive operations (J. org. Chem. 28, 2350 (1963)).

The industrial preparation of 4,4'-diamino-stilbene-2,2'-disulphonic acid has hitherto only been carried out by reduction of the corresponding dinitro acid with iron in acid solution. (H.E. Fierz David and L. Blangely, Grundlegende Operationen der Farbenchemie (Basic Operations in Dyestuff Chemistry), 5th edition (1943), page 163. In this process, the catalyst is obtained as an iron hydroxide sludge which is difficult to filter. In order to be able to dump this iron hydroxide sludge or pass it on to a process where it is utilised industrially, the sludge must first be worked up by drying or roasting. Catalytic reduction of 4,4'-dinitro-stilbene-2,2'-disulphonic acid has hitherto not been possible since the customary metallic hydrogenation catalysts do not reduce the nitro groups selectively but instead also reduce the C=C double bond.

The hydrogenation of nitrocinnamic acid esters to aminocinnamic acid esters is in principle possible with Raney nickel as the catalyst, but the absorption of hydrogen does not cease after reduction of the nitro group and instead continues. Industrially it is extremely difficult to determine the exact end point of the nitro reduction in the case of the hydrogenation of nitrocinnamic acids or nitrocinnamic acid esters, and to interrupt the reduction. Furthermore, only unsatisfactory yields, and products of insufficient purity, are obtained (E.K. Blaut and D.C. Silbermann, J. Am. Soc. 66, 1442 (1944)).

The absence of a generally satisfactory method for the selective hydrogenation of nitro groups alongside olefine bonds also emerges from a presentation by Rylander, according to which the selective hydrogenation is only possible in some cases with special steric circumstances, $PtO_2$ being recommended as the catalyst (Rylander: Catalytic Hydrogenation over Platinum Metals, N.Y. 1967, 178).

The same view as Rylander's is taken in "Katalytische Hydrierung im organisch chemischen Laboratorium" ("Catalytic Hydrogenation in Organic Chemistry Laboratories") (Enke Verlag 1965), page 90: "unsaturated amines are only obtained from a certain group in which the C-C double bond is difficult to attack by catalytically activated hydrogen, for steric and other reasons".

In some cases it is even possible to hydrogenate olefine bonds selectively, the nitro group remaining intact. According to G.V. Smith and J.A. Roth (Journal of Catalysis 4, 406 (1965)) the reduction of p-nitrophenyl acrylate on three different catalysts gives p-nitrophenyl propionate.

A particularly advantageous process for the preparation of aromatic amines which additionally still contain C-C multiple bonds has now been found, which is characterised in that aromatic nitro compounds which still contain C-C multiple bonds are hydrogenated, optionally in an inert solvent, in the presence of metal sulphides of the formula $$MeS_x$$

wherein $x$ is a number from 1 to 4 and

Me represents a metal atom of the group consisting of iron, nickel, ruthenium, rhodium, palladium, osmium, iridium, platinum and rhenium as catalysts, at 20° to 140° C, especially at 80° to 125° C and at 5 to 150 bars hydrogen pressure, especially at 10 to 80 bars hydrogen pressure.

Particularly suitable metals are iron, nickel, ruthenium, rhenium and platinum.

A preferred embodiment is characterised in that ruthenium sulphides or rhenium sulphides are used as catalysts.

The catalysts are in general added to the solution of the reducing aromatic nitro compound containing olefinic groups, but can also be produced before or during the reduction in this solution from a non-sulphidic metal salt, for example a chloride, carbonate, hydroxide, nitrate, oxide or sulphate, or a commercially available complex salt or the corresponding acid, such as $H_2(PtCl_6)$ or $Na_2(PtCl_6)$, and an alkali metal sulphide or polysulphide or alkaline earth metal sulphide or polysulphide. Rhenium sulphides are most suitably prepared from $NH_4ReO_4$.

It is also possible to treat finely divided metal, for example Raney nickel or Raney iron, with sulphur or a compound of divalent sulphur. To prepare the catalyst, the metal compounds and the sulphur compounds are employed in such ratio that the stoichiometric ratio of metal to sulphur is between 1 and 4, preferably between 2.0 and 3.5.

It is also possible to produce the catalytically active components by precipitating the metal as $MeS_x$ on an inert support, or treating precipitated metal on an inert support with sulphur or a suitable compound containing sulphur. A preliminary reduction with hydrogen is not necessary. A catalytically active component can be applied to suitable supports. For this purpose, the customary porous supports are used, such as are described in Ullmanns Enzyklopadie der technischen Chemie (Ullmanns Encyclopaedia of Industrial Chemistry), volume 9, page 263 et seq., Houben-Weyl, Methoden der organischen Chemie (Methods of Organic Chemistry), volume IV/2, page 147 et seq. and in Catalysis, vol. 1, page 251 et seq., Reinhold Publ., New York 1954. Examples which may be mentioned are active charcoals, aluminium oxide, silicon dioxide, aluminium silicates optionally in conjuction with alkali metal compounds and alkaline earth metal compounds, such as, for example, spinels, titanium dioxides and carbides such as silicon carbide and tungsten carbides, as well as organic materials such as silk and synthetic fibres. The catalysts are used in a pulverulent, suspended, particulate or moulded form. In a particular embodiment, one of the abovementioned metal sulphides is used on another metal sulphide as the support. $ReS_x$ on $NiS_x$ as the support may be mentioned as an example of this.

The amount of catalytically active metal sulphide on the support can be between 0.1 and 5% by weight, preferably 0.5 to 1% by weight.

The catalytically active component can be employed in amounts of 0.005 to 10.0%, especially 0.05 to 5%, relative to the nitro compound. The catalyst can be re-used for several hydrogenations. It can be advantageous to treat the used contact catalyst with an alkali metal sulphide solution before re-using it.

In a preferred embodiment of the process, the metal sulphide is first produced in the reduction solution. It is a particular advantage of this process that solutions of a metal salt on the one hand and a suitable sulphide compound, such as $Na_2S$, $Na_2S_x$, $Na_4S_x$ or $NaHS$, can be fed directly to the solution to be hydrogenated. In contrast to the solid catalysts, these solutions can easily be pumped even into reaction apparatuses which are already under pressure so that, for example, a continuous process, in which further catalyst is added continuously, can be carried out in a technically simple manner.

Suitable solvents are water, alcohols, ethers, hydrocarbons, chlorinated aromatic hydrocarbons, amides such as dimethylformamide and N-methylpyrrolidone, sulphones such as sulpholane, and nitriles. It is a particular advantage of the process that solvents, such as acetonitrile, which were insufficiently inert in the reductions hitherto customary, but which because of their high polarity are excellent solvents, can be employed.

A reduction in water, alcohols and alcohol-water mixtures is possible wherever the nitro compound to be reduced can be dissolved as a salt, for example in the case of 4,4'-dintrostilbene-2,2'-disulphonic acid.

The hydrogen used for the reduction can be pure hydrogen, for example electrolytic hydrogen. However, it is a particular advantage of the process that it is also possible to use hydrogen which because of impurities such as $H_2S$, $SO_2$, COS or CO is unsuitable for a reduction of nitro groups in the presence of other catalysts.

The process according to the invention is suitable for the selective catalytic reduction of nitro groups on an aromatic or quasi-aromatic ring in the presence of olefinic double bonds or triple bonds. One or more nitro groups can be present in the molecule. It is also possible selectively to reduce nitro compounds which contain several olefine bonds. The olefine bond can be present as an isolated bond in a carbon chain, in or on a cycloaliphatic ring, in or on a heterocyclic ring or on an aromatic ring. The olefine bond can be in conjugation with a carbonyl, carboxyl, nitrile, sulphone or phosphorus group. The olefine group can be monosubstituted, and can be, for example, an allyl or vinyl group. The group containing the olefine bond can be bonded directly to the aromatic or quasiaromatic ring which carries the nitro group which is to be reduced, or can be bonded via a sulphone, ether, thioether, carbonyl, carboxylic acid amide, carboxyl, amino, imino, imide, iminoimide or phenyl group or via a heterocyclic group. The heterocyclic group or the benzene group can be fused to the ring which carries the nitro group.

The compound can possess yet other substituents, such as Cl, Br, CN, amino, OH, alkoxy, SH, alkylmercapto, alkylcarbonyl or phenylcarbonyl, carboxyl, sulpho and alkylsulphonyl or phenylsulphonyl on the aromatic or quasi-aromatic ring and also on the radical carrying the olefine group.

Examples of aromatic nitro compounds with olefine groups which are suitable for the selective hydrogenation with metal sulphides as the catalyst are: 3-nitrocinnamic acid, 4-nitrocinnamic acid, 3-nitrocinnamic acid methyl ester, 3-nitrocinnamic acid ethyl ester, 4-nitrocinnamic acid methyl ester, 4-nitrocinnamic acid ethyl ester, 3-nitrocinnamic acid nitrile, 3-nitrocinnamic acid amide, 4-nitrobenzoic acid allyl ester, 3-nitrobenzoic acid allyl ester, 3-nitrobenzoic acid propargyl ester, 4-nitrobenzoic acid N-allylamide, 3-nitrobenzoic acid N-allylamide, 4-nitrobenzoic acid di-N-allylamide, 3-nitrobenzoic acid di-N-allylamide, 4nitrophthalic acid N-allylimide, 3nitrostyrene, tetrahydrophthalic acid (4-nitrophenyl)-imide, endomethylene-tetrahydrophthalic acid (4-nitrophenyl)-imide, 4,4'-dinitrostilbene-2,2'-disulphonic acid, N-(4-nitrophenyl)-acrylamide, N-(2-nitrophenyl)-methylacrylamide, 4-nitrophenyl acrylate, 4-nitrophenyl methylacrylate, 2-nitrophenyl methacrylate, 2-nitrophenyl acrylate, N-acryl-3-nitrocarbazole, 1-acryl-5-nitrobenzthiazole, 4-nitro-N-allyl-aniline, 2-nitro-N-allyl-aniline, (4-nitrophenyl)-diallylamine, 4-nitro-N-propargyl-aniline, 2-nitro-N-propargylaniline and 3-nitro-N-allylaniline.

The process is particularly suitable for the reduction of aromatic nitro compounds having a C-C double bond and especially for the reduction of 4,4'-dinitrostilbene-2,2'-disulphonic acid to 4,4'-diamino-silbene-2,2'-disulphonic acid.

To carry out the process, the aromatic nitro compound containing an olefine bond is dissolved or suspended in a suitable solvent. If in addition the compound contains an acid group, the process is suitably carried out in an aqueous alkaline solution. The catalyst is added to the solution or suspension in a customary pressure vessel, and hydrogenation is carried out under elevated pressure and, if appropriate, elevated temperature until the absorption of hydrogen has ceased. The reaction mixture is then separated from the catalyst by decanting, centrifuging or filtering, but is first rendered alkaline if acid reduction products are concerned. The catalyst can be used for further reactions.

The process of the invention can be realised industrially in different ways. For example it can be carried out as a sump phase hydrogenation according to Ullmanns Enzyklopadie der technischen Chemie (Ullmanns Encyclopaedia of Industrial Chemistry), volume 10, pages 508 and 560. For this purpose, the solution or suspension is passed through one or more successive reactors in the presence of the requisite catalyst. A possible procedure for this purpose is to pump the solution or suspension together with the catalyst through a stirred kettle cascade or a system of tubular ovens, if appropriate at elevated temperature and under elevated pressure. The catalyst required for the reaction can be supplied as fresh catalyst but it is more advantageous to re-use the catalyst, if necessary with addition of fresh catalyst.

The process can furthermore be carried out as a trickle phase hydrogenation.

Here, the solution of the nitro compounds is passed over a fixed catalyst, if appropriate at elevated temperature and under elevated pressure. The advantage of this process variant, described in Ullmanns Enzyklopadie der technischen Chemie (Ullmanns Encyclopaedia of Industrial Chemistry), volume 7, page 448, is that filtration of the catalyst is not required.

Solvents of high dissolving capacity, which in the presence of the customary hydrogenation catalysts are insufficiently inert, can be used. The catalyst has the advantage over most hydrogenation catalysts that it can be prepared in a very simple manner and acquires its active form under the conditions of the process according to the invention.

An expensive working-up stage, such as is made necessary, for example, by the iron reduction process, is hence superfluous. A further advantage in working up the reaction mixture is that the hydrogen which is still dissolved therein protects the amino compounds, which are very sensitive to oxygen, against the action of atmospheric oxygen.

The aromatic amino compounds obtained according to the process of the invention, which still contain at least one olefinic double bond, are valuable intermediate products for, for example, dyestuffs and optical brighteners.

Example 1

Preparation of the nickel sulphide catalyst 60 g of $Na_2S.9H_2O$ and 16 g of crystalline sulphur are heated in 375 ml of water at 90° C for 1 hour until complete solution has occurred. This solution is added dropwise at 90° C, over the course of 1 hour, to a solution of 66.3 g of $NiSO_4.6H_2O$ in 375 ml of water. The mixture is then heated for a further 30 minutes at the same temperature. The precipitate is filtered off and washed with 1 l of water in 5 portions. The catalyst thus obtained contains about 50% of water. 50 g of a water-moist paste of an industrially prepared disodium salt of 4,4'-dinitrostilbene-2,2'-disulphonic acid (containing 59% of free dinitrostilbenedisulphonic acid of molecular weight 430 and the following impurities per 100 g of solids, according to a thin layer chromatogram: 1.2 g of 4,4'-dinitrodibenzyl-2-disulphonic acid, 0.5 g of 4-nitrotoluene-2-sulphonic acid, <0.2 g of 4-nitrobenzaldehyde-2-sulphonic acid, 0.5 g of an unknown substance and 0.5 g of another unknown substance) are dissolved in 200 ml of water. To this solution are added 10 g of the catalyst described above and the mixture is introduced into a hydrogenation autoclave of 700 ml capacity. The hydrogenation is carried out under a hydrogen pressure of 150 bars at 100° C over the course of 60 minutes. The drop in the hydrogen pressure is throughout compensated by adding further hydrogen to restore the initial pressure. After the reaction, the pressure is released and the reaction mixture is filtered. The filtrate is light yellow and has a pH of 8.0 The analysis of the filtrate shows a content of 10.5% of 4,4'-diaminostilbene-2,2'-disulphonic acid containing the following impurities determined by thin layer chromatography (g in 100 g of 100% strength material): 0.5 g of 4,4'-diaminodibenzyl-2,2'-disulphonic acid, 0.2 g of 4-aminotoluene-2-sulphonic acid, 0.5 g of 4-aminobenzaldehyde-2-sulphonic acid and 0.3 g of unknown compounds. Nitro compounds are no longer detectable by titration with $TiCl_3$.

Example 2

50 g of 4,4'-dinitrostilbene-2,2'-disulphonic acid are hydrogenated as in Example 1, but the catalyst recovered from Example 1 is used. The filtrate obtained after the hydrogenation is light yellow, has a pH of 8.0 and contains 10.6% of 4,4'-diaminostilbene-2,2'-disulphonic acid.

The impurities amount to the following (g in 100 g of 100% strength material): 1.0 g of 4,4'-diaminodibenzyl-2,2'-disulphonic acid, 0.1 g of 4-aminotoluene-2-sulphonic acid and 1.0 g of 4-aminobenzaldehyde-2-sulphonic acid. The catalyst recovered is used in a further batch with 50 g of 4,4'-dinitrostilbene-2,2'-disulphonic acid. Result:

The filtrate is a pale reddish-coloured solution of pH 8.0 containing 11.0% in addition to the following impurities (g in 100 g of 100% strength material): 1.0 g of 4,4'-diaminodibenzyl-2,2'-disulphonic acid, 0.1 g of 4-aminotoluene-2-sulphonic acid and 1.0 g of 4-aminobenzaldehyde-2-sulphonic acid. Nitro compounds are not detectable.

Example 3

Preparation of the rhenium sulphide catalyst 10 g of ammonium perrhenate (69.4% Re) are dissolved in 200 ml of water at 80° C. After adding 13.2 g of concentrated hydrochloric acid, 45 g of 18.5% strength aqueous NaHS solution are allowed to run in over the course of 30 minutes at the same temperature. The catalyst precipitate is allowed to settle and the supernatant solution is sucked off.

50 g of a water-moist paste of the disodium salt of 4,4'-dinitrosilbene-2,2'-disulphonic acid, of 54.6% strength expressed as free disulphonic acid, and containing the following impurities (g in 100 g of 100% strength material): 0.5 g of 4,4'-dinitrodibenzyl-2,2'-disulphonic acid, <0.2 g of 4-nitrotoluene-2-sulphonic acid and <0.2 g of 4-nitrobenzaldehyde-2-sulphonic acid, are dissolved in 200 ml of water and 10 g of the catalyst sludge described above are added. The reaction mixture is hydrogenated over the course of 60 minutes in the manner described in Example 1. After the hydrogenation, the catalyst is allowed to settle out. The decanted solution is light yellow and has a pH of 8.0 and a solids content of 10.2% of the corresponding diaminodisulphonic acid, together with the following impurities (g in 100 g of 100% strength material): 0.5 g of 4,4'-diaminodibenzyl-2,2'-disulphonic acid, 0.3 g of 4-aminotoluene-2-sulphonic acid and 1.0 g of 4-aminobenzaldehyde-2-sulphonic acid. Nitro compounds are no longer detectable.

Example 4

50 g of 4,4'-dinitrostilbene-2,2'-disulphonic acid are hydrogenated with the catalyst recovered from Example 3, analogously to Example 1. A light yellow solution of pH 8.0 is obtained, with 10.9% solids content of diamino compound containing the following impurities (g in 100 g of 100% strength material): 1.0 g of 4,4'-diaminodibenzyl-2,2'-disulphonic acid, 0.2 g of 4-aminotoluene-2-sulphonic acid and 0.5 g of 4-aminobenzaldehyde-2-sulphonic acid. Nitro compounds are no longer detectable.

The catalyst is again recovered and used in a further batch with 50 g of 4,4'-dinitrostilbene-2,2'-disulphonic acid. The reaction is carried out analogously to Example 1.

The resulting solution is light yellow, has a pH of 8.0 and contains 10.0% of diamino compound with the following impurities (g in 100 g of 100% strength material): 1.0 g of 4,4'-diaminodibenzyl-2,2'-disulphonic acid, 0.1 g of 4-aminotoluene-2-sulphonic acid and 0.5 g of 4-aminobenzaldehyde-2-sulphonic acid. Nitro compounds are no longer detectable.

Example 5

Preparation of the ruthenium sulphide catalyst 20 g of ruthenium chloride (35% of Ru) are dissolved in 200 ml of water at 90° C. A mixture of 33 g of $Na_2S.9H_2O$ and 2.2 g of sulphur in 200 g of water is run into this solution at 90° C over the course of 30 minutes. The reaction is allowed to continue for 30 minutes at this temperature and the precipitate is filtered off and washed with about 2.5 l of water.

50 g of the dinitrostilbenedisulphonic acid described in Example 3 are dissolved in 200 g of water. 10 g of the ruthenium sulphide catalyst are added. The mixture is hydrogenated as in Example 1. However, the reaction time is only 10 minutes. After filtering, a light yellow solution of pH 8.0 is obtained, containing 9.4% of diamino compound with the following impurities (g in 100 g of 100% strength material): 1.0 g of 4,4'-diaminodibenzyl-2,2'-disulphonic acid, 0.2 g of 4-aminotoluene-2-sulphonic acid and 0.3 g of 4-aminobenzaldehyde-2-sulphonic acid. Nitro compounds are no longer detectable.

The catalyst filtered off is re-used for the hydrogenation of a further 50 g of 4,4'-dinitrostilbene-2,2'-disulphonic acid.

However, the reaction time is 25 minutes and the temperature is 50° C. A light yellow solution containing 10.2% of diamino compound, which contains the following impurities (g of 100% strength material) is obtained: 1.0 g of 4,4'-diaminodibenzyl-2,2'disulphonic acid, 0.1 g of 4-aminotoluene-2-sulphonic acid and 0.5 g of 4-aminobenzaldehyde-2-sulphonic acid.

Example 6

50 g of the dinitrostilbenedisulphonic acid mentioned in Example 1 are dissolved in 200 ml of water. 2 g of a commercially available platinum sulphide catalyst (Engelhard Ind.; sold through Karl Roth No. 2-3610) are added to this solution, the catalyst having the following composition: 2.54% of platinum, 0.75% of sulphur, 50.00% of water, remainder active charcoal, loss on ignition = 94.54%.

This mixture is hydrogenated over the course of 15 minutes at 50° C and 150 bars. The pressure is then maintained for a further 10 minutes at the same temperature. The catalyst is filtered off and a pale reddish-coloured solution of pH 8.0 is obtained. This contains 10.2% of diamino compound with the following impurities (g in 100 g of 100% strength material): 0.5 g of 4,4'-diaminodibenzyl-2,2'-disulphonic acid, 0.1 g of 4-aminotoluene-2-sulphonic acid and 1.0 g of 4-aminobenzaldehyde-2-sulphonic acid.

A further 50 g of dinitrostilbene-acid are hydrogenated with the catalyst which has been filtered off. A reddish solution of pH 8.0 is obtained, having the following composition:

Content of diamino compound: 10.5%, impurities (g in 100 g of 100% strength material): 1.0 g of 4,4'-diaminodibenzyl-2,2'-disulphonic acid, 0.1 g of 4-aminotoluene-2-sulphonic acid and 0.5-1 g of 4-aminobenzaldehyde-2-sulphonic acid.

Example 7

Preparation of the iron sulphide catalyst

A mixture of 60 g of $Na_2S.9H_2O$ and 16 g of sulphur in 375 ml of water is allowed to run into a solution of 70.1 g of $FeSO_4.7H_2O$ in 375 ml of water at 90° C over the course of 1 hour and the mixture is heated to 90° C for a further hour until complete solution has occurred.

The iron sulphide precipitate is filtered off and rinsed with 2.5 l of water.

10 g of the iron sulphide catalyst described above are added to 50 g of the dinitrostilbenedisulphonic acid described in Example 1, in 140 g of water and 60 g of methanol. The mixture is hydrogenated at 100° C and 125 bars hydrogen pressure over the course of 2 hours. The catalyst is then filtered off. The solution is reddish and has pH 8.0. The content of diamino compound is 10.5% with the following impurities (g in 100 g of 100% strength material): 0.5 g of 4,4'-diaminodibenzyl-2,2'-disulphonic acid, 0.1 g of 4-aminotoluene-2-sulphonic acid and 6-7 g of 4-aminobenzaldehyde-2-sulphonic acid. Nitro compounds are no longer detectable.

Example 8

Example 1 is repeated with a solution of 4,4'-dinitrostilbene-2,2'-disulphonic acid dissolved in a mixture of 140 ml of water and 60 ml of methanol. The hydrogenation time is 2 hours.

On filtration, a yellow solution is obtained, containing 10.5% of diamino compound and the following impurities (g in 100 g of 100% strength material): 0.5 g of 4,4'-diamino-dibenzyl-2,2'-disulphonic acid, 0.2 g of 4-aminotoluene-2-sulphonic acid and 0.2 g of 4-aminobenzaldehyde-2-sulphonic acid. Nitro compounds are not longer detectable.

The catalyst which has been filtered off is re-used to hydrogenate a further batch of 50 g of the dinitrostilbenedisulphonic acid mentioned in Example 1, in 200 ml of water. A light yellow solution of pH 8.0 is obtained, containing 10.6% of diamino compound and the following impurities (g in 100 g of 100% strength material): 1.0 g of 4,4'-diaminodibenzyl-2,2'-disulphonic acid, 0.1 g of 4-aminotoluene-2-sulphonic acid and 1.0 g of 4-aminobenzaldehyde-2-sulphonic acid. Nitro compounds are no longer detectable.

Example 9

Preparation of the ruthenium sulphide catalyst on active charcoal.

3.3 g of $Na_2S.9H_2O$ and 0.22 g of crystalline sulphur in 200 ml of water are heated at 90° C for 1 hour until complete solution has taken place. 34.3 g a commercially available active charcoal (internal surface area, determined by the BET method, 800 m²/g; 80% of this charcoal have a particle size of less than 40 μm) are added to this solution. A solution of 2 g of ruthenium chloride (35% Ru) in 200 ml of water is added dropwise at 90° C over the course of 5 minutes. The reaction mixture is then filtered. The filter residue is washed with 5 portions of water each of 100 ml.

50 g of dinitrostilbenedisulphonic acid as used in Example 3 are dissolved in 200 ml of water and hydrogenated in 2 hours in the presence of 5 g of the catalyst described above, at 100° C and 150 bars hydrogen pressure. After filtration, a yellow solution of pH 8.0 is obtained, containing 4,4'-diaminostilbene-2,2'-disulphonic acid and the following impurities (g in 100 g of 100% strength material): 1.5% of 4,4'-diaminodibenzyl-2,2'-disulphonic acid, 0.1% of 4-aminotoluene-2-sulphonic acid and 0.2% of 4-aminobenzaldehyde-2-sulphonic acid. Nitro compounds are no longer detectable.

The catalyst which has been filtered off is re-used to hydrogenate four further batches each of 50 g of 4,4'-dinitrostilbene-2,2'-disulphonic acid (batches $b - e$).

| Additive No. | Reduction time [mins.] | Colour of the solution | Content of diamino compound [%] | 4,4'-diamino-dibenzyl-2,2'-disulphonic acid | 4-amino-toluene-2-sulphonic acid | 4-amino-benzaloe-hyde-2-sulphonic acid |
|---|---|---|---|---|---|---|
| b | 120 | light yellow | 10.2 | 0.5–1.0 | <0.1 | 0.5–1.0 |
| c | 120 | yellow | 10.1 | 0.5–1.0 | <0.1 | 0.5–1.0 |
| d[1] | 60 | yellow | 10.0 | 0.5–1.0 | <0.1 | 0.2 |
| e[1] | 30 | yellow | 10.1 | 0.1–1.0 | <0.1 | 1.0 |

[1]In the last two batches, about 0.1 g of nitro compound per 100 g of 100% strength material is detectable in the filtrate.

Example 10

3-Aminocinnamic acid methyl ester 50 g of 3-nitrocinnamic acid methyl ester in 350 ml of methanol are hydrogenated in the presence of 1.5 g of the platinum sulphide catalyst described in Example 6 (5% strength on active charcoal) for 2 hours at 70° C and one half hour at 80° C under 130 bars hydrogen pressure in a stirred autoclave of 700 ml capacity. The pressure drop has ceased after 2 hours. The solution is freed from the catalyst and evaporated. 43 g of crystalline 3-aminocinnamic acid methyl ester of melting point 75° C are obtained.

In the nuclear resonance spectrum, the signals characteristic of the olefine bond are to be found at 6.35 ppm and 7.6 ppm. Signals for an ethylene grouping are absent.

Example 11

35 g of 2-nitro-N-allylaniline in 400 ml of methanol are hydrogenated in the presence of 1.5 g of the catalyst described in Example 6, at 75° C and 100-120 bars of hydrogen, for 1.5 hours, to give N-allyl-o-phenylenediamine. The solution which has been freed from the catalyst by filtration is distilled.

The liquid which boils at 75°–80° C and 0.2 mm Hg, of $n_D^{20}$ 1.5922, shows signals at 6 ppm and 5 ppm for the protons of the allyl double bond in the nuclear resonance spectrum. Signals for a propyl group are not detectable.

We claim:

1. Process for the preparation of an aromatic amine which contains an olefinic double bond which comprises hydrogenating an aromatic nitro compound containing an olefinic double bond in the presence of a catalyst consisting essentially of a metal sulphide of the formula $MeS_x$ in which $x$ is a number from 1 to 4 and Me is iron, nickel, ruthenium, rhodium, palladium, rhenium, osmium, iridium or platinum at 20° to 140° C and at 5 to 150 bars hydrogen pressure.

2. Process of claim 1 in which said catalyst is employed in an amount of 0.005 to 10.0% by weight relative to said nitro compound.

3. Process according to claim 1, characterised in that Me represents iron, nickel, ruthenium, rhenium or platinum.

4. Process according to claim 1, characterised in that Me represents ruthenium or rhenium.

5. Process according to claim 1, characterised in that the hydrogenation is carried out at 80° to 125° C and 10 to 80 bars hydrogen pressure.

6. Process according to claim 1, characterised in that $x$ represents a number from 2 to 3.5.

7. Process according to claim 1, for the preparation of 4,4'-diaminostilbene-2,2'-disulphonic acid from 4,4'-dinitrostilbene-2,2'-disulphonic acid.

* * * * *